(12) United States Patent
Fram et al.

(10) Patent No.: US 10,614,615 B2
(45) Date of Patent: *Apr. 7, 2020

(54) SYSTEMS AND METHODS FOR VIEWING MEDICAL 3D IMAGING VOLUMES

(71) Applicant: MERGE HEALTHCARE SOLUTIONS INC., Hartland, WI (US)

(72) Inventors: Evan K. Fram, Paradise Valley, AZ (US); Murray A. Reicher, Rancho Santa Fe, CA (US)

(73) Assignee: MERGE HEALTHCARE SOLUTIONS INC., Hartland, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/292,006

(22) Filed: Oct. 12, 2016

(65) Prior Publication Data

US 2017/0046870 A1 Feb. 16, 2017

Related U.S. Application Data

(63) Continuation of application No. 14/081,225, filed on Nov. 15, 2013, now Pat. No. 9,501,863, which is a continuation of application No. 13/535,758, filed on Jun. 28, 2012, now Pat. No. 8,610,746, which is a continuation of application No. 13/079,597, filed on Apr. 4, 2011, now Pat. No. 8,217,966, which is a
(Continued)

(51) Int. Cl.
*G06T 15/08* (2011.01)
*A61B 6/00* (2006.01)
*G06T 3/40* (2006.01)
*G06T 19/00* (2011.01)
*G06T 19/20* (2011.01)
*A61B 90/00* (2016.01)

(52) U.S. Cl.
CPC ............ *G06T 15/08* (2013.01); *A61B 6/5223* (2013.01); *A61B 90/37* (2016.02); *G06T 3/40* (2013.01); *G06T 19/00* (2013.01); *G06T 19/20* (2013.01); *A61B 2090/367* (2016.02); *G06T 2210/41* (2013.01); *G06T 2219/008* (2013.01)

(58) Field of Classification Search
None
See application file for complete search history.

(56) References Cited

U.S. PATENT DOCUMENTS 4,672,683 A 6/1987 Matsueda
5,123,056 A 6/1992 Wilson
(Continued)

FOREIGN PATENT DOCUMENTS

WO WO 2007/131157 11/2007

OTHER PUBLICATIONS

US 7,801,341 B2, 09/2010, Fram et al. (withdrawn)
(Continued)

*Primary Examiner* — Joni Richer
(74) *Attorney, Agent, or Firm* — Michael Best & Friedrich LLP

(57) ABSTRACT

A method of automatically tracking the portions of a 3D medical imaging volume, such as the voxels, that have already been displayed according to use-defined display parameters, notating those portions, and providing the user with information indicating what portions of the imaging volume have been displayed at full resolution.

12 Claims, 6 Drawing Sheets

Related U.S. Application Data continuation of application No. 11/268,262, filed on Nov. 3, 2005, now Pat. No. 7,920,152.

(60) Provisional application No. 60/625,690, filed on Nov. 4, 2004.

(56) References Cited

U.S. PATENT DOCUMENTS

| | | |
|---|---|---|
| 5,172,419 A | 12/1992 | Manian |
| 5,179,651 A | 1/1993 | Taaffe et al. |
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,867,322 A | 2/1999 | Morton |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Argiro |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,211,795 B1 * | 4/2001 | Izuta .............. G08B 5/227 340/7.52 |
| 6,211,884 B1 | 4/2001 | Knittel et al. |
| 6,219,059 B1 | 4/2001 | Argiro |
| 6,219,061 B1 | 4/2001 | Lauer et al. |
| 6,243,095 B1 | 6/2001 | Shile et al. |
| 6,243,098 B1 | 6/2001 | Lauer et al. |
| 6,262,740 B1 | 7/2001 | Lauer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Lauer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Lauer et al. |
| 6,424,346 B1 | 7/2002 | Correll et al. |
| 6,424,996 B1 | 7/2002 | Killcommons et al. |
| 6,426,749 B1 | 7/2002 | Knittel et al. |
| 6,427,022 B1 | 7/2002 | Craine et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,678,764 B2 | 1/2004 | Parvelescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,785,410 B2 | 8/2004 | Vining et al. |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,504 B1 | 4/2006 | Argiro et al. |
| 7,031,846 B2 | 4/2006 | Kaushikkar et al. |
| 7,039,723 B2 | 5/2006 | Hu et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,123,684 B2 | 10/2006 | Jing et al. |
| 7,136,064 B2 | 11/2006 | Zuiderveld |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,209,578 B2 | 4/2007 | Saito et al. |
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,516,417 B2 | 4/2009 | Amador et al. |
| 7,523,505 B2 | 4/2009 | Menschik et al. |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,574,029 B2 | 8/2009 | Peterson et al. |

(56) References Cited

U.S. PATENT DOCUMENTS

| | | |
|---|---|---|
| 7,583,861 B2 | 9/2009 | Hanna et al. |
| 7,590,272 B2 | 9/2009 | Brejl et al. |
| 7,599,534 B2 | 10/2009 | Krishnan |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,413 B2 | 2/2010 | Partovi et al. |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,941,462 B2 | 5/2011 | Akinyemi et al. |
| 7,953,614 B1 | 5/2011 | Reicher |
| 7,970,188 B2 | 6/2011 | Mahesh et al. |
| 7,970,625 B2 | 6/2011 | Reicher et al. |
| 7,991,210 B2 | 8/2011 | Peterson et al. |
| 7,995,821 B2 | 8/2011 | Nakamura |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,262,572 B2 | 9/2012 | Chono |
| 8,292,811 B2 | 10/2012 | Relkuntwar et al. |
| 8,298,147 B2 | 10/2012 | Huennekens et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,520,978 B2 | 8/2013 | Jakobovits |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,771,189 B2 | 7/2014 | Ionasec et al. |
| 8,797,350 B2 | 8/2014 | Fram |
| 8,879,807 B2 | 11/2014 | Fram et al. |
| 8,913,808 B2 | 12/2014 | Reicher et al. |
| 8,954,884 B1 | 2/2015 | Barger |
| 8,976,190 B1 | 3/2015 | Westerhoff et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,536,324 B1 | 1/2017 | Fram |
| 9,542,082 B1 | 1/2017 | Reicher et al. |
| 9,672,477 B1 | 6/2017 | Reicher et al. |
| 9,684,762 B2 | 6/2017 | Reicher et al. |
| 9,727,938 B1 | 8/2017 | Reicher et al. |
| 9,734,576 B2 | 8/2017 | Fram et al. |
| 9,754,074 B1 | 9/2017 | Reicher et al. |
| 9,836,202 B1 | 12/2017 | Reicher et al. |
| 9,892,341 B2 | 2/2018 | Reicher et al. |
| 9,934,568 B2 | 4/2018 | Reicher et al. |
| 1,009,611 A1 | 10/2018 | Fram et al. |
| 1,015,768 A1 | 12/2018 | Reicher et al. |
| 10,387,612 B2 | 8/2019 | Wu et al. |
| 10,437,444 B2 | 10/2019 | Reicher et al. |
| 10,438,352 B2 | 10/2019 | Fram et al. |
| 2001/0016822 A1 | 8/2001 | Bessette |
| 2001/0041991 A1 | 11/2001 | Segal et al. |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0054038 A1 | 5/2002 | Nemoto |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0099273 A1 | 7/2002 | Bocionek et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0110285 A1 | 8/2002 | Wang et al. |
| 2002/0144697 A1 | 10/2002 | Betz |
| 2002/0145941 A1 | 10/2002 | Poland et al. |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0188637 A1 | 12/2002 | Bailey et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0053668 A1 | 3/2003 | Ditt et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140044 A1 | 7/2003 | Mok et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215120 A1 | 11/2003 | Uppaluri et al. |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |
| 2004/0027359 A1 | 2/2004 | Aharon et al. |
| 2004/0061889 A1 | 4/2004 | Wood et al. |
| 2004/0068170 A1 | 4/2004 | Wang et al. |
| 2004/0077952 A1 | 4/2004 | Rafter et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |

(56) References Cited

U.S. PATENT DOCUMENTS

| | | |
|---|---|---|
| 2004/0122705 A1 | 6/2004 | Sabol et al. |
| 2004/0122787 A1 | 6/2004 | Avinash et al. |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0203775 A1 | 9/2005 | Chesbrough |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0259118 A1 | 11/2005 | Mojaver |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111937 A1 | 5/2006 | Yarger et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0238546 A1 | 10/2006 | Handley et al. |
| 2006/0239573 A1 | 10/2006 | Novatzky et al. |
| 2006/0241979 A1 | 10/2006 | Sato et al. |
| 2006/0267976 A1 | 11/2006 | Saito et al. |
| 2006/0274145 A1 | 12/2006 | Reiner |
| 2006/0276708 A1 | 12/2006 | Peterson et al. |
| 2006/0277075 A1 | 12/2006 | Salwan |
| 2006/0282408 A1 | 12/2006 | Wisely et al. |
| 2006/0282447 A1 | 12/2006 | Hollebeek |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2007/0245308 A1 | 10/2007 | Hill et al. |
| 2007/0270695 A1 | 11/2007 | Keen |
| 2008/0016111 A1 | 1/2008 | Keen |
| 2008/0021877 A1 | 1/2008 | Saito et al. |
| 2008/0031507 A1 | 2/2008 | Uppaluri et al. |
| 2008/0059245 A1 | 3/2008 | Sakaida et al. |
| 2008/0097186 A1 | 4/2008 | Biglieri et al. |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1 | 5/2008 | Sadikali et al. |
| 2008/0130966 A1 | 6/2008 | Crucs |
| 2008/0133526 A1 | 6/2008 | Haitani et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0028410 A1 | 1/2009 | Shimazaki |
| 2009/0080719 A1 | 3/2009 | Watt |
| 2009/0091566 A1 | 4/2009 | Turney et al. |
| 2009/0094513 A1 | 4/2009 | Bay |
| 2009/0123052 A1 | 5/2009 | Ruth et al. |
| 2009/0129643 A1 | 5/2009 | Natanzon et al. |
| 2009/0129651 A1 | 5/2009 | Zagzebski et al. |
| 2009/0132586 A1 | 5/2009 | Napora et al. |
| 2009/0150481 A1 | 6/2009 | Garcia et al. |
| 2009/0164247 A1 | 6/2009 | Dobler et al. |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0326373 A1 | 12/2009 | Boese et al. |
| 2010/0053353 A1 | 3/2010 | Hunter et al. |
| 2010/0086182 A1 | 4/2010 | Hui |
| 2010/0131887 A1 | 5/2010 | Salazar-Ferrer et al. |
| 2010/0138239 A1 | 6/2010 | Reicher et al. |
| 2010/0198608 A1 | 8/2010 | Kaboff et al. |
| 2010/0201714 A1 | 8/2010 | Reicher et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram et al. |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0293162 A1 | 12/2011 | Pajeau |
| 2011/0316873 A1 | 12/2011 | Reicher et al. |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0183191 A1 | 7/2012 | Nakamura |
| 2012/0194540 A1 | 8/2012 | Reicher et al. |

(56) References Cited

U.S. PATENT DOCUMENTS

| | | |
|---|---|---|
| 2012/0196258 A1 | 8/2012 | Geijsen et al. |
| 2012/0208592 A1 | 8/2012 | Davis et al. |
| 2012/0284657 A1 | 11/2012 | Hafey et al. |
| 2012/0320093 A1 | 12/2012 | Zhu et al. |
| 2013/0070998 A1 | 3/2013 | Shibata |
| 2013/0076681 A1 | 3/2013 | Sirpal et al. |
| 2013/0083023 A1 | 4/2013 | Fram |
| 2013/0129198 A1 | 5/2013 | Sherman et al. |
| 2013/0129231 A1 | 5/2013 | Dale et al. |
| 2013/0159019 A1 | 6/2013 | Reicher |
| 2013/0169661 A1 | 7/2013 | Reicher et al. |
| 2013/0195329 A1 | 8/2013 | Canda et al. |
| 2013/0198682 A1 | 8/2013 | Matas et al. |
| 2013/0297331 A1 | 11/2013 | Zuehlsdorff et al. |
| 2014/0022194 A1 | 1/2014 | Ito |
| 2014/0096049 A1 | 4/2014 | Vonshak et al. |
| 2014/0119514 A1 | 5/2014 | Miyazawa |
| 2014/0142983 A1 | 5/2014 | Backhaus et al. |
| 2014/0378810 A1 | 12/2014 | Davis et al. |
| 2015/0046349 A1 | 2/2015 | Michael, Jr. et al. |
| 2015/0101066 A1 | 4/2015 | Fram |
| 2015/0363104 A1 | 12/2015 | Ichioka et al. |
| 2016/0034110 A1 | 2/2016 | Edwards |
| 2016/0270746 A1 | 9/2016 | Foos et al. |
| 2017/0038951 A1 | 2/2017 | Reicher et al. |
| 2017/0039321 A1 | 2/2017 | Reicher et al. |
| 2017/0039322 A1 | 2/2017 | Reicher et al. |
| 2017/0039350 A1 | 2/2017 | Reicher et al. |
| 2017/0039705 A1 | 2/2017 | Fram et al. |
| 2017/0046014 A1 | 2/2017 | Fram |
| 2017/0046483 A1 | 2/2017 | Reicher et al. |
| 2017/0046485 A1 | 2/2017 | Reicher et al. |
| 2017/0046495 A1 | 2/2017 | Fram |
| 2017/0046870 A1 | 2/2017 | Fram |
| 2017/0053404 A1 | 2/2017 | Reicher et al. |
| 2017/0200064 A1 | 7/2017 | Reicher et al. |
| 2017/0200269 A1 | 7/2017 | Reicher et al. |
| 2017/0200270 A1 | 7/2017 | Reicher et al. |
| 2017/0206324 A1 | 7/2017 | Reicher et al. |
| 2017/0239720 A1 | 8/2017 | Levin et al. |
| 2017/0293720 A1 | 10/2017 | Reicher et al. |
| 2017/0301090 A1 | 10/2017 | Fram et al. |
| 2017/0308647 A1 | 10/2017 | Reicher et al. |
| 2018/0059918 A1 | 3/2018 | Reicher et al. |
| 2018/0225824 A1 | 8/2018 | Fram et al. |

OTHER PUBLICATIONS

US 8,208,705 B2, 06/2012, Reicher et al. (withdrawn)
Notice of Allowance from the U.S. Patent and Trademark Office for U.S. Appl. No. 15/631,313 dated Jan. 30, 2018 (10 pages).
Office Action from the U.S. Patent and Trademark Office for U.S. Appl. No. 15/346,530 dated Mar. 26, 2018 (40 pages).
Office Action from the U.S. Patent and Trademark Office for U.S. Appl. No. 15/799,657 dated Mar. 8, 2018 (25 pages).
U.S. Appl. No. 14/540,830, Systems and Methods for Viewing Medical Images, filed Nov. 13, 2014.
U.S. Appl. No. 15/254,627, Systems and Methods for Interleaving Series of Medical Images, filed Sep. 1, 2016.
U.S. Appl. No. 14/095,123, Systems and Methods for Retrieval of Medical Data, filed Dec. 3, 2013.
U.S. Appl. No. 14/244,431, Systems and Methods for Matching, Naming, and Displaying Medical Images, filed Apr. 3, 2014.
U.S. Appl. No. 14/298,806, Smart Placement Rules, filed Jun. 6, 2013.
U.S. Appl. No. 11/942,687, Smart Forms, filed Nov. 19, 2007.
U.S. Appl. No. 14/043,165, Automated Document Filings, filed Oct. 1, 2013.
U.S. Appl. No. 11/944,000, Exam Scheduling With Customer Configured Notifications, filed Nov. 21, 2007.
U.S. Appl. No. 13/768,765, System and Method of Providing Dynamic and Customizable Medical Examination Forms, filed Feb. 15, 2013.
U.S. Appl. No. 15/163,600, Rules-Based Approach to Transferring and/or Viewing Medical Images, filed May 24, 2016.
U.S. Appl. No. 14/792,210, Dynamic Montage Reconstruction, filed Jul. 6, 2015.
U.S. Appl. No. 15/140,346, Database Systems and Interactive User Interfaces for Dynamic Interaction With, and Sorting of, Digital Medical Image Data, filed Apr. 27, 2016.
U.S. Appl. No. 15/140,363, Database Systems and Interactive User Interfaces for Dynamic Interation With, and Comparison of, Digital Medical Image Data, filed Apr. 27, 2016.
U.S. Appl. No. 15/140,351, Database Systems and Interactive User Interfaces for Dynamic Interaction With, and Review of, Digital Medical Image DA, filed Apr. 27, 2016.
U.S. Appl. No. 15/140,348, Database Systems and Interactive User Interfaces for Dynamic Interaction With, and Indications of, Digital Medical Image Data, filed Apr. 27, 2016.
U.S. Appl. No. 14/081,225, filed Nov. 15, 2013 including its ongoing prosecution history, including without limitation Office Actions, Amendments, Remarks, and any other potentially relevant documents, Fram et al.
U.S. Appl. No. 12/437,522, filed May 7, 2009, Fram.
U.S. Appl. No. 14/792,210, filed Jul. 6, 2015 including its ongoing prosecution history, including without limitation Office Actions, Amendments, Remarks, and any other potentially relevant documents., Reicher.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Office Action dated Dec. 11, 2013, in U.S. Appl. No. 13/477,853.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated Jan. 25, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated Jan. 20, 2016, in U.S. Appl. No. 14/502,055.

(56) References Cited

OTHER PUBLICATIONS

Interview Summary dated Apr. 14, 2016, in U.S. Appl. No. 14/502,055.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Office Action dated Mar. 3, 2015 in U.S. Appl. No. 14/095,123.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Feb. 23, 2016 in U.S. Appl. No. 14/095,123.
Final Office Action dated Jul. 20, 2016 in U.S. Appl. No. 14/095,123.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Corrected Notice of Allowance dated Jun. 27, 2016, in U.S. Appl. No. 14/502,055.
Office Action dated Mar. 10, 2016 in U.S. Appl. No. 14/081,225.
Notice of Allowance dated Sep. 2, 2016 in U.S. Appl. No. 14/081,225.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated Mar. 18, 2016 in U.S. Appl. No. 14/244,431.
Interview Summary dated Jun. 17, 2016 in U.S. Appl. No. 14/244,431.
Notice of Allowance dated Aug. 18, 2016 in U.S. Appl. No. 14/244,431.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Final Office Action, dated Jun. 17, 2015 in U.S. Appl. No. 14/298,806.
Office Action, dated Feb. 16, 2016 in U.S. Appl. No. 14/298,806.
Final Office Action, dated Jul. 21, 2016 in U.S. Appl. No. 14/298,806.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Final Office Action, dated Jan. 5, 2015 in U.S. Appl. No. 11/942,687.
Interview Summary, dated Mar. 4, 2015 in U.S. Appl. No. 11/942,687.
PTAB Examiner's Answer, dated Feb. 25, 2016 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Office Action dated Oct. 14, 2014 in U.S. Appl. No. 14/043,165.
Final Office Action dated Apr. 1, 2015 in U.S. Appl. No. 14/043,165.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Board Decision dated Mar. 23, 2016 in U.S. Appl. No. 11/944,000.
Office Action, dated Jul. 15, 2016 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 17, 2015 in U.S. Appl. No. 13/768,765.
Interview Summary dated Jun. 11, 2015 in U.S. Appl. No. 13/768,765.
Notice of Allowance dated Aug. 28, 2015 in U.S. Appl. No. 13/768,765.
Notice of Allowability dated Nov. 20, 2015 in U.S. Appl. No. 13/768,765.
Notice of Allowability dated Jul. 28, 2016 in U.S. Appl. No. 13/768,765.

(56) References Cited

OTHER PUBLICATIONS

Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Aug. 13, 2015 in U.S. Appl. No. 14/687,853.
Notice of Allowance dated Feb. 25, 2016 in U.S. Appl. No. 14/687,853.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
Agfa HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
Agfa HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
Aspyra's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 (Jun. 2007); pp. 105-113.
Erickson, et al.: "Image Registration Improves Confidence and Accuracy of Image Interpretation," Special Issue-Imaging Informatics, Cancer Informatics 2007: 1 19-24, May 2007.
Fujifilm Medical Systems, Synapse® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, Synapse® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, Synapse® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.

(56) References Cited

OTHER PUBLICATIONS

Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Mendelson, et al., "Informatics in Radiology—Image Exchange: IHE and the Evolution of Image Sharing," RadioGraphics, Nov.-Dec. 2008, vol. 28, No. 7.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Rosset et al.: "OsiriX: An Open-Source Software for Navigating in Multidimensional DICOM Images," Journal of digital Imaging, Sep. 2004, pp. 205-216.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Schellingerhout, Dawid, MD, et al.: "Coregistration of Head CT Comparison Studies: Assessment of Clinical Utility," Acad Radiol 2003; 10:242-248, Mar. 2003.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516, Oct. 2009.
Tahmoush, D. and Samet, H., A New Database for Medical Images and Information, 2007, Medical Imaging 2007; PACS and Imaging Informatics, vol. 6516. pp. 1-9, Feb. 2007.
Correct Notice of Allowability from the U.S. Patent and Trademark Office for U.S. Appl. No. 15/631,313 dated Jul. 20, 2018 (3 pages).
Notice of Allowance from the U.S. Patent and Trademark Office for U.S. Appl. No. 15/799,657 dated Aug. 15, 2018 (8 pages).
Office Action from the U.S. Patent and Trademark Office for U.S. Appl. No. 15/945,448 dated Jul. 16, 2018 (7 pages).
U.S. Appl. No. 15/346,530, Systems and Methods for Matching, Naming, and Displaying Medical Images, filed Nov. 8, 2016.
U.S. Appl. No. 15/292,014, System and Method of Providing Dynamic and Customizable Medical Examination for, filed Oct. 12, 2016.
U.S. Appl. No. 15/292,023, Selective Display of Medical Images, filed Oct. 12, 2016.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
Office Action dated Jan. 17, 2017, in U.S. Appl. No. 14/540,830.
Office Action dated Dec. 12, 2016, in U.S. Appl. No. 15/254,627.
Corrected Notice of Allowance dated Oct. 21, 2016 in U.S. Appl. No. 14/081,225.
Corrected Notice of Allowance dated Nov. 16, 2016 in U.S. Appl. No. 14/244,431.
Appeal Brief dated Jul. 15, 2016 in U.S. Appl. No. 14/043,165.
Examiner's Answer dated Nov. 14, 2016, in U.S. Appl. No. 14/043,165.

(56) References Cited

OTHER PUBLICATIONS

Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
Notice of Allowance from the U.S. Patent and Trademark Office for U.S. Appl. No. 15/945,448 dated Jan. 10, 2019 (9 pages).
Notice of Allowance from the U.S. Patent and Trademark Office for U.S. Appl. No. 15/631,313 dated May 25, 2018 (10 pages).
Examiner Interview Summary from the U.S. Patent and Trademark Office for U.S. Appl. No. 11/179,384 dated Feb. 18, 2009 (2 page).
Examiner Interview Summary from the U.S. Patent and Trademark Office for U.S. Appl. No. 11/179,384 dated Sep. 24, 2008 (4 page).
Notice of Allowance from the U.S. Patent and Trademark Office for U.S. Appl. No. 14/540,830 dated Aug. 15, 2017 (11 pages).
Final Office Action from the U.S. Patent and Trademark Office for U.S. Appl. No. 14/540,830 dated May 15, 2017 (42 pages).
Applicant-Initiated Interview Summary from the U.S. Patent and Trademark Office for U.S. Appl. No. 14/540,830 dated Jul. 28, 2017 (3 page).
Applicant-Initiated Interview Summary from the U.S. Patent and Trademark Office for U.S. Appl. No. 14/540,830 dated Mar. 24, 2017 (3 page).
Non-Final Office Action from the U.S. Patent and Trademark Office for U.S. Appl. No. 15/292,006 dated May 9, 2018 (17 pages).
Final Office Action from the U.S. Patent and Trademark Office for U.S. Appl. No. 15/346,530 dated Sep. 6, 2018 (14 pages).
Applicant-Initiated Interview Summary from the U.S. Patent and Trademark Office for U.S. Appl. No. 15/346,530 dated May 17, 2018 (3 page).
Patent Board Decision from the U.S. Patent and Trademark Office for U.S. Appl. No. 11/942,687 dated Dec. 22, 2017 (13 page).
Interview Summary from the U.S. Patent and Trademark Office for U.S. Appl. No. 11/942,687 dated Jun. 10, 2011 (3 page).
Patent Board Decision from the U.S. Patent and Trademark Office for U.S. Appl. No. 14/043,165 dated Dec. 20, 2017 (11 page).
Notice of Allowance from the U.S. Patent and Trademark Office for U.S. Appl. No. 14/043,165 dated Aug. 6, 2018 (11 pages).
Notice of Allowance from the U.S. Patent and Trademark Office for U.S. Appl. No. 14/043,165 dated Mar. 19, 2018 (11 pages).
Non-Final Office Action from the U.S. Patent and Trademark Office for U.S. Appl. No. 15/475,930 dated Sep. 7, 2018 (16 pages).
Non-Final Office Action from the U.S. Patent and Trademark Office for U.S. Appl. No. 15/475,930 dated Jan. 10, 2018 (11 pages).
Final Office Action from the U.S. Patent and Trademark Office for U.S. Appl. No. 15/475,930 dated Jun. 1, 2018 (17 pages).
Notice of Allowance from the U.S. Patent and Trademark Office for U.S. Appl. No. 15/469,342 dated Nov. 30, 2017 (11 pages).
Non-Final Office Action from the U.S. Patent and Trademark Office for U.S. Appl. No. 15/469,342 dated Jun. 27, 2017 (62 pages).
Examiner-Initiated Interview Summary from the U.S. Patent and Trademark Office for U.S. Appl. No. 15/469,342 dated Nov. 30, 2017 (1 page).
Applicant-Initiated Interview Summary from the U.S. Patent and Trademark Office for U.S. Appl. No. 15/469,342 dated Dec. 13, 2017 (3 page).
Non-Final Office Action from the U.S. Patent and Trademark Office for U.S. Appl. No. 15/469,281 dated Apr. 2, 2018 (59 pages).
Non-Final Office Action from the U.S. Patent and Trademark Office for U.S. Appl. No. 15/469,281 dated Jun. 26, 2017 (51 pages).
Final Office Action from the U.S. Patent and Trademark Office for U.S. Appl. No. 15/469,281 dated Sep. 20, 2018 (58 pages).
Final Office Action from the U.S. Patent and Trademark Office for U.S. Appl. No. 15/469,281 dated Jan. 11, 2018 (60 pages).
Applicant-Initiated Interview Summary from the U.S. Patent and Trademark Office for U.S. Appl. No. 15/469,281 dated Jun. 26, 2018 (3 page).
Applicant-Initiated Interview Summary from the U.S. Patent and Trademark Office for U.S. Appl. No. 15/469,281 dated Oct. 13, 2017 (3 page).
Notice of Allowance from the U.S. Patent and Trademark Office for U.S. Appl. No. 15/469,296 dated Jan. 22, 2018 (11 pages).
Non-Final Office Action from the U.S. Patent and Trademark Office for U.S. Appl. No. 15/469,296 dated Jun. 27, 2017 (58 pages).
Applicant-Initiated Interview Summary from the U.S. Patent and Trademark Office for U.S. Appl. No. 15/469,296 dated Oct. 13, 2017 (3 page).
Non-Final Office Action from the U.S. Patent and Trademark Office for U.S. Appl. No. 15/188,872 dated Oct. 19, 2018 (12 pages).
Non-Final Office Action from the U.S. Patent and Trademark Office for U.S. Appl. No. 15/188,819 dated Jul. 3, 2018 (7 pages).
Non-Final Office Action from the U.S. Patent and Trademark Office for U.S. Appl. No. 15/140,351 dated Jul. 30, 2018 (25 pages).
Final Office Action from the U.S. Patent and Trademark Office for U.S. Appl. No. 15/140,351 dated Dec. 6, 2018 (21 pages).
Non-Final Office Action from the U.S. Patent and Trademark Office for U.S. Appl. No. 15/140,348 dated Nov. 19, 2018 (33 pages).
Examiner-Initiated Interview Summary from the U.S. Patent and Trademark Office for U.S. Appl. No. 12/857,915 dated Jul. 3, 2014 (1 page).
Corrected Notice of Allowability from the U.S. Patent and Trademark Office for U.S. Appl. No. 15/254,627 dated Jul. 13, 2017 (4 page).
Notice of Allowance from the U.S. Patent and Trademark Office for U.S. Appl. No. 15/254,627 dated Apr. 3, 2017 (11 pages).
Notice of Allowance from the U.S. Patent and Trademark Office for U.S. Appl. No. 11/265,979 dated May 13, 2011 (14 pages).
Examiner-Initiated Interview Summary from the U.S. Patent and Trademark Office for U.S. Appl. No. 13/171,081 dated Sep. 4, 2013 (1 page).
Notice of Allowance from the U.S. Patent and Trademark Office for U.S. Appl. No. 14/095,123 dated Mar. 30, 2017 (10 pages).
Notice of Allowance from the U.S. Patent and Trademark Office for U.S. Appl. No. 12/870,645 dated Sep. 13, 2011 (8 pages).
Applicant Summary of Interview of Examiner from the U.S. Patent and Trademark Office for U.S. Appl. No. 13/345,606 dated Oct. 21, 2013 (8 pages).
Notice of Allowance from the U.S. Patent and Trademark Office for U.S. Appl. No. 14/298,806 dated Apr. 12, 2017 (10 pages).
Notice of Allowance from the U.S. Patent and Trademark Office for U.S. Appl. No. 11/944,000 dated Jan. 30, 2017 (12 pages).
Non-Final Office Action from the U.S. Patent and Trademark Office for U.S. Appl. No. 11/944,000 dated Oct. 5, 2012 (11 pages).
Interview Summary from the U.S. Patent and Trademark Office for U.S. Appl. No. 11/944,000 dated Feb. 4, 2011 (3 page).
Examiner-Initiated Interview Summary from the U.S. Patent and Trademark Office for U.S. Appl. No. 13/768,765 dated Aug. 28, 2015 (1 page).
Examiner-Initiated Interview Summary from the U.S. Patent and Trademark Office for U.S. Appl. No. 12/891,543 dated Nov. 14, 2013 (1 page).
Applicant-Initiated Interview Summary from the U.S. Patent and Trademark Office for U.S. Appl. No. 14/179,328 dated Dec. 11, 2014 (3 page).
Examiner-Initiated Interview Summary from the U.S. Patent and Trademark Office for U.S. Appl. No. 15/163,600 dated Sep. 14, 2016 (1 page).
Notice of Allowance from the U.S. Patent and Trademark Office for U.S. Appl. No. 15/292,023 dated Apr. 11, 2014 (11 pages).
Applicant-Initiated Interview Summary from the U.S. Patent and Trademark Office for U.S. Appl. No. 15/469,342 dated Oct. 13, 2017 (3 page).

(56) References Cited

OTHER PUBLICATIONS

Notice of Allowance from the U.S. Patent and Trademark Office for U.S. Appl. No. 15/469,296 dated Janaury 22, 2018 (11 pages).
Corrected Notice of Allowability from the U.S. Patent and Trademark Office for U.S. Appl. No. 13/572,397 dated Jun. 29, 2015 (2 pages).
Patent Board Decision from the U.S. Patent and Trademark Office for U.S. Appl. No. 12/437,522 dated Sep. 5, 2017 (12 pages).
Notice of Allowance from the U.S. Patent and Trademark Office for U.S. Appl. No. 12/437,522 dated Apr. 23, 2014 (11 pages).
Non-Final Office Action from the U.S. Patent and Trademark Office for U.S. Appl. No. 12/437,522 dated Sep. 10, 2014 (4 pages).
Non-Final Office Action from the U.S. Patent and Trademark Office for U.S. Appl. No. 12/437,522 dated Feb. 3, 2011 (16 pages).
Final Office Action from the U.S. Patent and Trademark Office for U.S. Appl. No. 12/437,522 dated Apr. 20, 2015 (5 pages).
Final Office Action from the U.S. Patent and Trademark Office for U.S. Appl. No. 12/437,522 dated Oct. 14, 2011 (17 pages).
Examiner's Answer to Appeal Brief from the U.S. Patent and Trademark Office for U.S. Appl. No. 12/437,522 dated Jul. 5, 2016 (18 pages).
Interview Summary from the U.S. Patent and Trademark Office for U.S. Appl. No. 12/437,522 dated Jun. 1, 2011 (3 page).
Applicant-Initiated Interview Summary from the U.S. Patent and Trademark Office for U.S. Appl. No. 12/437,522 dated Aug. 11, 2015 (3 page).
Notice of Allowance from the U.S. Patent and Trademark Office for U.S. Appl. No. 15/799,657 dated Feb. 6, 2019 (8 pages).
Non-Final Office Action from the U.S. Patent and Trademark Office for U.S. Appl. No. 15/292,014 dated Jan. 24, 2019 (7 pages).
Corrected Notice of Allowability from the U.S. Patent and Trademark Office for U.S. Appl. No. 15/469,281 dated Mar. 4, 2019 (8 pages).
Notice of Allowance from the U.S. Patent and Trademark Office for U.S. Appl. No. 15/469,281 dated Janaury 11, 2019 (12 pages).
Corrected Notice of Allowability from the U.S. Patent and Trademark Office for U.S. Appl. No. 15/945,448 dated Feb. 20, 2019 (2 pages).
Notice of Allowance from the U.S. Patent and Trademark Office for U.S. Appl. No. 15/945,448 dated May 6, 2019 (7 pages).
Final Office Action from the U.S. Patent and Trademark Office for U.S. Appl. No. 15/188,872 dated May 8, 2019 (14 pages).
Notice of Allowance from the U.S. Patent and Trademark Office for U.S. Appl. No. 15/346,530 dated May 15, 2019 (8 pages).
Corrected Notice of Allowability from the U.S. Patent and Trademark Office for U.S. Appl. No. 15/945,448 dated Jul. 15, 2019 (2 pages).
Non-Final Office Action from the U.S. Patent and Trademark Office for U.S. Appl. No. 15/140,346 dated May 28, 2019 (39 pages).
Non-Final Office Action from the U.S. Patent and Trademark Office for U.S. Appl. No. 15/140,348 dated Jul. 7, 2019 (21 pages).
Non-Final Office Action from the U.S. Patent and Trademark Office for U.S. Appl. No. 15/140,363 dated Jun. 3, 2019 (33 pages).
Non-Final Office Action from the U.S. Patent and Trademark Office for U.S. Appl. No. 15/140,351 dated May 21, 2019 (14 pages).
Notice of Allowance from the U.S. Patent and Trademark Office for U.S. Appl. No. 15/346,530 dated Aug. 27, 2019 (7 pages).
Non-Final Office Action from the U.S. Patent and Trademark Office for U.S. Appl. No. 15/646,756 dated Jul. 16, 2019 (12 pages).
Final Office Action from the U.S. Patent and Trademark Office for U.S. Appl. No. 15/475,930 dated Apr. 1, 2019 (18 pages).
Notice of Allowance from the U.S. Patent and Trademark Office for U.S. Appl. No. 15/292,014 dated Jul. 11, 2019 (8 pages).
Notice of Allowance from the U.S. Patent and Trademark Office for U.S. Appl. No. 15/469,281 dated Aug. 19, 2019 (11 pages).
Notice of Allowance from the U.S. Patent and Trademark Office for U.S. Appl. No. 15/469,281 dated Apr. 29, 2019 (10 pages).
Notice of Allowance from the U.S. Patent and Trademark Office for U.S. Appl. No. 15/188,872 dated Aug. 23, 2019 (10 pages).
Notice of Allowance from the U.S. Patent and Trademark Office for U.S. Appl. No. 15/188,819 dated Jan. 25, 2019 (7 pages).
Notice of Allowability from the U.S. Patent and Trademark Office for U.S. Appl. No. 15/188,819 dated Mar. 15, 2019 (5 pages).
Notice of Allowance from the U.S. Patent and Trademark Office for U.S. Appl. No. 15/188,819 dated Aug. 21, 2019 (8 pages).
Notice of Allowance from the U.S. Patent and Trademark Office for U.S. Appl. No. 15/799,657 dated May 20, 2019 (8 pages).
Corrected Notice of Allowability from the U.S. Patent and Trademark Office for U.S. Appl. No. 15/945,448 dated Aug. 28, 2019 (2 pages).
Notice of Allowance from the U.S. Patent and Trademark Office for U.S. Appl. No. 14/792,210 dated Jun. 17, 2019 (10 pages).
Non-Final Office Action from the U.S. Patent and Trademark Office for U.S. Appl. No. 15/631,291 dated Oct. 8, 2019 (12 pages).
Corrected Notice of Allowability from the U.S. Patent and Trademark Office for U.S. Appl. No. 15/346,530 dated Oct. 9, 2019 (4 pages).
Supplemental Notice of Allowability from the U.S. Patent and Trademark Office for U.S. Appl. No. 15/188,872 dated Oct. 28, 2019 (5 pages).
Supplemental Notice of Allowability from the U.S. Patent and Trademark Office for U.S. Appl. No. 15/188,819 dated Oct. 2, 2019 (4 pages).
Notice of Allowance from the U.S. Patent and Trademark Office for U.S. Appl. No. 15/292,014 dated Nov. 15, 2019 (7 pages).
Non-Final Office Action from the U.S. Patent and Trademark Office for U.S. Appl. No. 16/529,378 dated Oct. 22, 2019 (8 pages).
Final Office Action from the U.S. Patent and Trademark Office for U.S. Appl. No. 15/140,346 dated Oct. 31, 2019 (41 pages).
Final Office Action from the U.S. Patent and Trademark Office for U.S. Appl. No. 15/140,351 dated Nov. 14, 2019 (14 pages).
Non-Final Office Action from the U.S. Patent and Trademark Office for U.S. Appl. No. 15/140,348 dated Dec. 4, 2019 (21 pages).
Notice of Allowance from the U.S. Patent and Trademark Office for U.S. Appl. No. 14/792,210 dated Oct. 11, 2019 (9 pages).

\* cited by examiner

SYSTEMS AND METHODS FOR VIEWING MEDICAL 3D IMAGING VOLUMES

CROSS-REFERENCE TO RELATED APPLICATIONS

This application is a continuation of U.S. application Ser. No. 14/081,225, filed Nov. 15, 2013, entitled "SYSTEMS AND METHODS FOR VIEWING MEDICAL 3D IMAGING VOLUMES," which is a continuation of U.S. application Ser. No. 13/535,758, filed Jun. 28, 2012, entitled "SYSTEMS AND METHODS FOR VIEWING MEDICAL 3D IMAGING VOLUMES," now U.S. Pat. No. 8,610,746, which is a continuation of U.S. application Ser. No. 13/079,597, filed Apr. 4, 2011, entitled "SYSTEMS AND METHODS FOR VIEWING MEDICAL 3D IMAGING VOLUMES," now U.S. Pat. No. 8,217,966, which is a continuation of U.S. application Ser. No. 11/268,262, filed Nov. 3, 2005, entitled "SYSTEMS AND METHODS FOR VIEWING MEDICAL 3D IMAGING VOLUMES," now U.S. Pat. No. 7,920,152, which claims priority under 35 U.S.C. § 119(e) to U.S. Provisional Application Ser. No. 60/625,690, filed on Nov. 4, 2004, each of which is hereby expressly incorporated by reference in its entirety.

BACKGROUND OF THE INVENTION

Field of the Invention

This invention relates to management and viewing of medical images and, more particularly, to systems and methods of tracking which portions of three dimensional imaging volumes have been displayed using predetermined display parameters.

Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. Accordingly, there is a need for improved systems and methods of viewing and manipulating these digital images.

For projection modalities like mammography and radiography, information may be represented in digital images in the form of a two dimensional array of pixels (picture elements). Other techniques are capable of creating cross sectional views of the body, such as magnetic resonance imaging (MRI), computed tomography (CT), and positron emission computed tomography (PET). With these techniques, the information in an image represents a two-dimensional slice of the body, with each pixel in the image representing information from a small volume in space, a voxel (volume element). In a typical imaging exam ("scan") using these modalities, a series of parallel images are acquired through the body. The information in this series of images therefore represents a 3D volume of space or imaging volume. In addition, a three-dimensional imaging volume may be created from a set of nonparallel images as well. It is also possible to perform a three-dimensional acquisition directly with some modalities. Thus, the image volume may be generated by a device that creates a 3D data set.

While a radiologist or physician interpreting such an imaging volume might choose to view the acquired images, the plane in which the images were acquired may not be optimal for accurate and efficient analysis and interpretation of the scan. For example, imaging might be performed in the axial plane with the patient asymmetrically positioned in the scanner. The resulting images would therefore not be in the axial plane with respect to the patient's anatomy. In that case, a new set of axial images would be desired that were in the axial plane with respect to the patient's anatomy. Alternatively, structures of interest might be best evaluated in other planes, such as coronal, sagittal or oblique planes.

A reader may choose to view the information in planes that differ from the plane in which the images were originally acquired as a supplement or substitute for viewing the original images. Those of skill in the art will recognize that given the 3D imaging volume created by the original images from the imaging device, a new set of 2D images that slice up the imaging volume along other axes using multiplanar reformatting (MPR) may be created. The reformatting could be used to create a series of images in another axis prior to viewing or the viewer might choose to interactively create new views in real time as part of his analysis of the information.

No matter how the reader chooses to view the imaging volume acquired by the scan, all the acquired relevant information in the imaging volume should be viewed. Currently available systems for viewing imaging volumes do not provide a mechanism for tracking which portions of the imaging volume, such as which voxels of the imaging volume, have been displayed on a display device. Thus, the viewer must independently determine which portions of an imaging volume have been viewed. As those of skill in the art will recognize, requiring the viewer to determine when all relevant portions of an imaging volume have been viewed introduces the possibility that portions of the imaging volume are not viewed and, thus, features and/or abnormalities expressed in the unviewed portions may not be detected. Systems and methods for tracking and alerting a viewer of an imaging volume which portions of the imaging volume have been viewed are desired.

SUMMARY OF THE INVENTION

One embodiment comprises a computing system for viewing an imaging volume comprising a plurality of planar images that represent portions of an imaged object. Each of the planar images comprises a plurality of voxels. The system comprises a display device configured to display a predetermined number of pixels. The system also comprises an input interface configured to receive the imaging volume. The system also comprises an application module being configured to initiate display of one or more navigation images in one or more navigation planes. The navigation images are displayed at a reduced resolution so that the entire navigation images may be viewed on the display device. The application module is configured to initiate generation of a reformatted image comprising voxels that are along any plane determined by the user. In one embodiment, a portion of the navigation image corresponding to voxels that have been displayed at full resolution in any plane are visually distinguishable from the remaining portions of the navigation image.

Another embodiment comprises a system for viewing a three dimensional imaging volume. The system comprises: at least one three dimensional imaging volume; and a module configured to provide an interface to allow a user to selectively display portions of the imaging volume, wherein the module automatically determines whether at least a region of the three dimensional imaging volume has been displayed at a particular resolution.

Another embodiment comprises a system for viewing a three dimensional imaging volume. The system comprises: at least one three dimensional imaging volume; and means for selectively displaying portions of the image of the display, wherein the displaying means automatically determines whether at least a region of the three dimensional imaging volume has been displayed at a particular resolution.

Yet another embodiment comprises a method of viewing a 3D imaging volume on a display device coupled to a computing system. The display device is configured to concurrently display one or more navigation images and one of a plurality of reformatted images that comprise a plane of the imaging volume along any axis chosen by the view. The method comprises receiving an imaging volume at the computing system, wherein the imaging volume comprises a plurality of voxels arranged in a three dimensional array. The method also comprises displaying on the display device one or more navigation images comprising voxels of the imaging volume. The method also comprises selecting a portion of the navigation image and generating a reformatted image comprising voxels of the imaging volume from a second plane of the imaging volume. In one embodiment, the first and second planes intersect at the selected portion of the navigation image. The method also comprises displaying on the display device the reformatted image and updating the navigation image to include a visual indication that the selected portion of the navigation image has been displayed on the display device.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
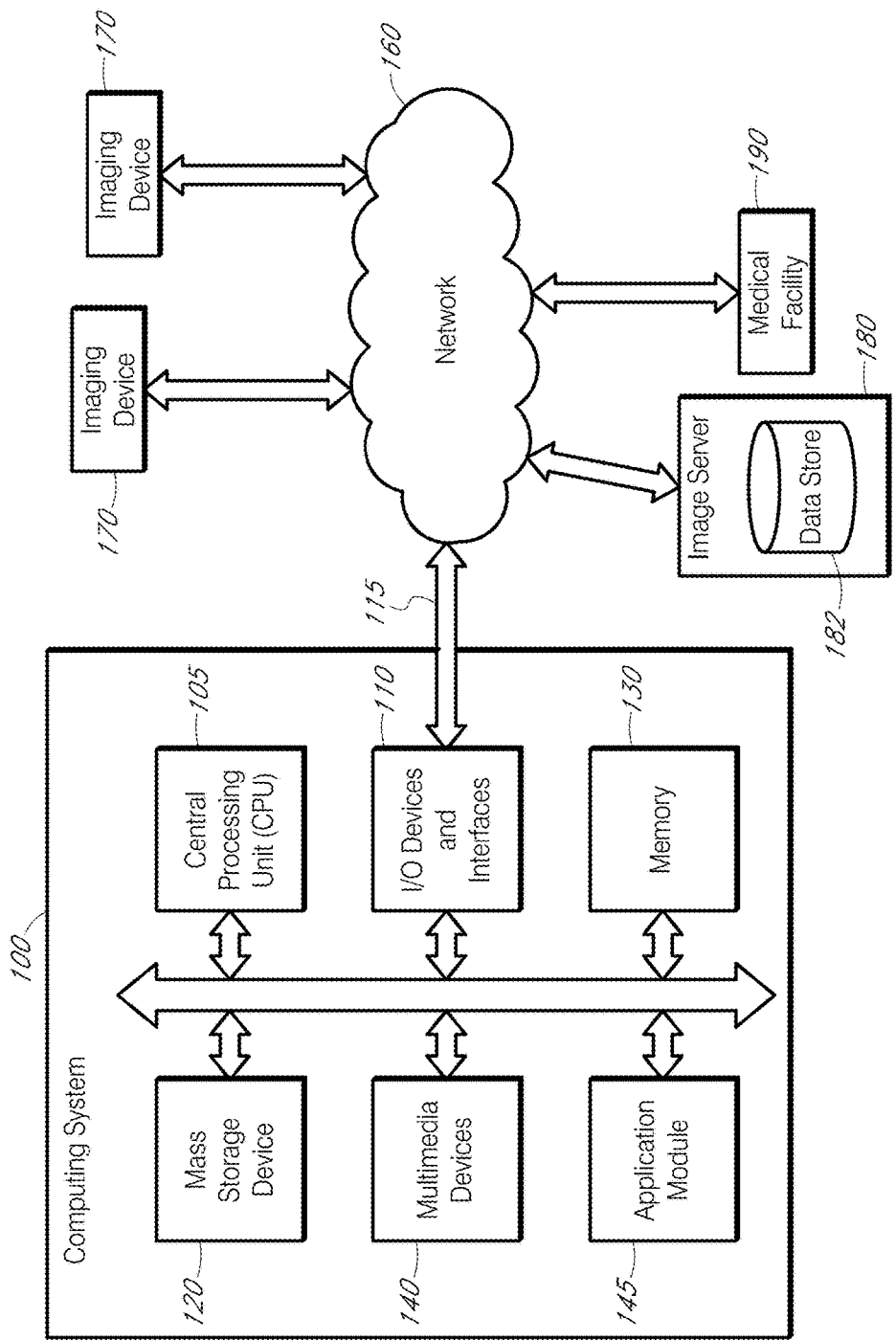
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server 180 via the network 160 and image information is transmitted to the image server 180 and stored in the data store 182. In one embodiment, the image data is stored in Digital Imaging and Communications in Medicine ("DICOM") format. The complete DICOM specifications may be found on the National Electrical Manufactures Association Website at <medical.nema.org>. Also, NEMA PS 3—*Digital Imaging and Communications in Medicine,* 2004 ed., Global Engineering Documents, Englewood Colo., 2004, provides an overview of the DICOM standard. Each of the above-cited references is hereby incorporated by reference in their entireties. In one embodiment, the data store 182 also stores the user-defined display parameters associated with one or more of the images stored on the data store 182. As discussed in further detail below, the user-defined display parameters may vary depending of the type of image, area imaged, clinical indication, source of image, display device, user, or other factors. Accordingly, any type of user-defined display parameter is expressly contemplated for use in conjunction with the systems and methods described herein.

The exemplary image server 180 is configured to store images from multiple sources and in multiple formats. For example, the image server 180 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

Definition of Terms

Below is a definition of certain terms used herein.

"Modality" is defined as a medical imaging device (a patient who undergoes an MRI is said to have been examined or scanned with the MRI modality).

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, geologic mapping, and satellite images, for example.

"Patient" refers to an individual who undergoes a medical imaging examination.

"3D Imaging Volume" or "Imaging Volume" refers to the information acquired by an imaging device (also referred to as a "scanner") in the form of images that together form a 3D volume of digital information representative of the volume that was scanned, such as a portion of a patient.

"Viewing" is defined to include the process of visually observing one or more medical images associated with exams.

"Viewer" is defined as any person who views a medical image.

"Reading" is defined to include the process of visually observing one or more medical images for the purpose of creating a professional medical report, also called an interpretation. When reading is complete, an exam may be labeled "read," indicating that the medical professional has completed observation of the one or more medical images for purposes of creating a medical report.

"Reader" is defined to include one who is authorized to perform the reading process.

"User" is defined to include any person that is a viewer and/or a reader.

"Display parameters" are defined to include methods of display of an image or exam. For example, an image or exam may be displayed with a certain pixel window level or width (similar to brightness and contrast), in color, based on a certain color map, opacity map, or other display parameters.

"Full voxel display" is defined to include display on a monitor or other display system of information from every voxel of a 3D imaging volume.

"Full Resolution" is defined to include the concurrent display of all voxels of a 3D imaging volume.

"Reduced Resolution" is defined to include display of less than all of the voxels of a 3D imaging volume.

"User-defined display parameter" refers to rules that a user can establish and store in a database that establish criteria for image display that is considered adequate. For example, a user-defined display parameter might store a rule that triggers certain warnings or displays if all voxels have not been displayed or, alternatively, if at least a predetermined portion of the voxels have not been displayed with a certain display method (such as image window, level, brightness, contrast, opacity, color look-up table, or other parameters). User-defined display parameters may also refer to other image processing functions, such as edge enhancement and automated image analysis functions, e.g., computer-aided detection (CAD) techniques.

As noted above, some medical imaging scanners, such as computed tomography (CT) and Magnetic Resonance Imaging (MRI), are capable of collecting a series of adjacent 2D images through a region of interest that, when stacked up, represent a 3D imaging volume. In some cases, a three-dimensional volume is directly acquired. For example, each individual two-dimensional image might consist of 512×512 pixels (picture elements), with each pixel representing a 1 mm×1 mm×1 mm voxel (volume element) within the region scanned, although the dimensions of the voxel need not be equal. If 1,000 such contiguous images were acquired then these images would then form an imaging volume consisting of 512×512×1,000 voxels representing a volume of space that is 51.2 cm×51.2 cm×100 cm in size.

Figure 2A:
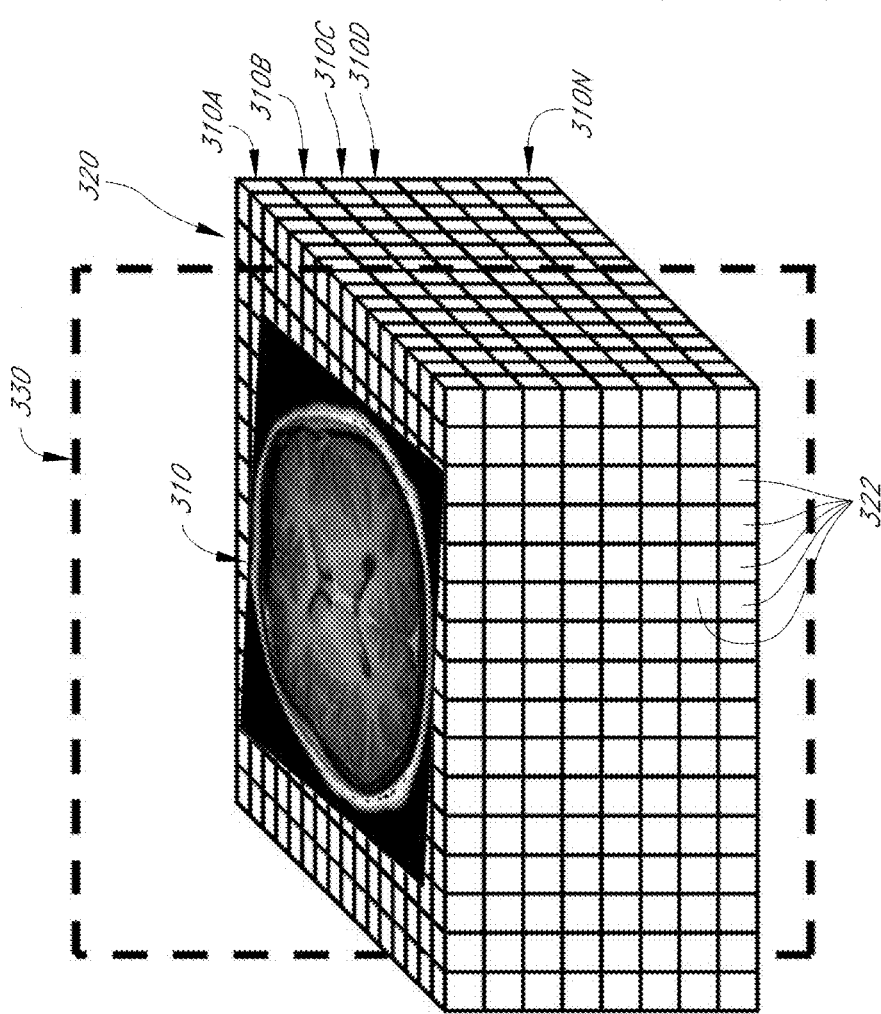
FIG. 2A is a three-dimensional depiction of an imaging volume comprising a plurality of voxels.
Figure 2B:
FIG. 2B illustrates a reformatted image generated from the imaging volume of FIG. 2A.

FIG. 2A is a three-dimensional depiction of an imaging volume 320 comprising a plurality of voxels 322. In the embodiment of FIG. 2A, a series of contiguous axial MRI images 310A-310N of a brain are stacked to yield the 3D imaging volume 320. In certain embodiments, the orientation of the scanned images with respect to the patient is arbitrary, as images from any orientation can be stacked to form a 3D imaging volume, such as imaging volume 320. Once an imaging volume is created, 2D images can be created in any plane through the imaging volume using, for example, a technique known as multiplanar reformatting. In the embodiment of FIG. 2B, two-dimensional images in the coronal orientation 330 may be generated from the imaging volume 320, even though the original 2D images 310 were collected in the axial plane. Thus, coronal images, such as coronal image 340 may be generated for viewing. The coronal image 340 comprises voxels from each of the source images 310A-310N at the predetermined plane. In one embodiment, images may be reformatted from any arbitrary oblique plane of the imaging volume 320. This is often useful to physicians interpreting imaging volumes as particular features of anatomy and pathology may be best appreciated in a particular imaging plane.

Figure 3B:
FIG. 3B is a reformatted image in the sagittal plane that was generated from the imaging volume described with respect to FIG. 3A.
Figure 3A:
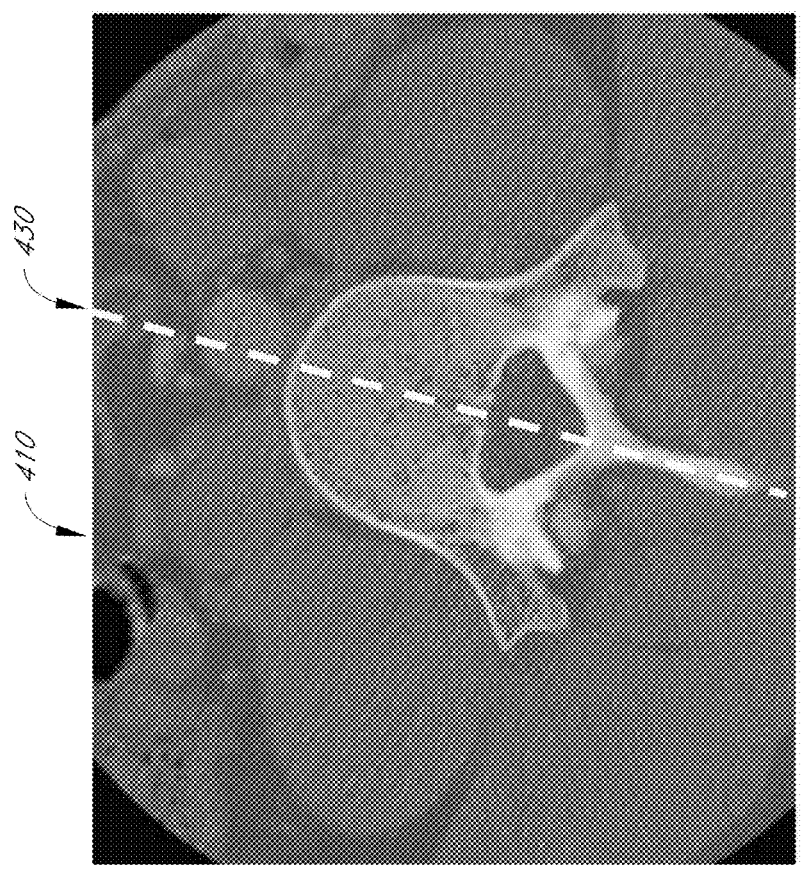
FIG. 3A is a CT image of a patient's lumbar spine in the axial plane taken from an imaging volume comprising a plurality of axial images.

FIG. 3A is a CT image 410 of a patient's lumbar spine in the axial plane taken from an imaging volume comprising a plurality of axial images. FIG. 3B is a reformatted image 420 from the imaging volume in the sagittal plane. As those of skill in the art will appreciate, assessment of alignment of the vertebral bodies may be best appreciated in the sagittal plane. Accordingly, sagittal images, including image 420 may be created from the axial imaging volume using multiplanar reformatting. In the embodiment of FIG. 3A, the patient is rotated with respect to the scanner and, thus, creation of images that are in the true sagittal plane with respect to the patient's spine require that the images be reformatted along an oblique axis 430.

As described above, the process of multiplanar reformatting allows generation of reformatted images from imaging volumes in planes other than the plane in which the original images were acquired. Therefore, a viewer of an imaging volume may choose to view the source images acquired from the imaging device and/or reformatted images, reformatted to be in a plane that differs from the plane of the source images. No matter whether the viewer is viewing source images or reformatted images, it may be important that the viewer examines the entire imaging volume so that important features of the exam are appreciated. In addition, it may be important that voxels of the imaging volume are displayed according to a predefined set of display parameters.

Figure 4:
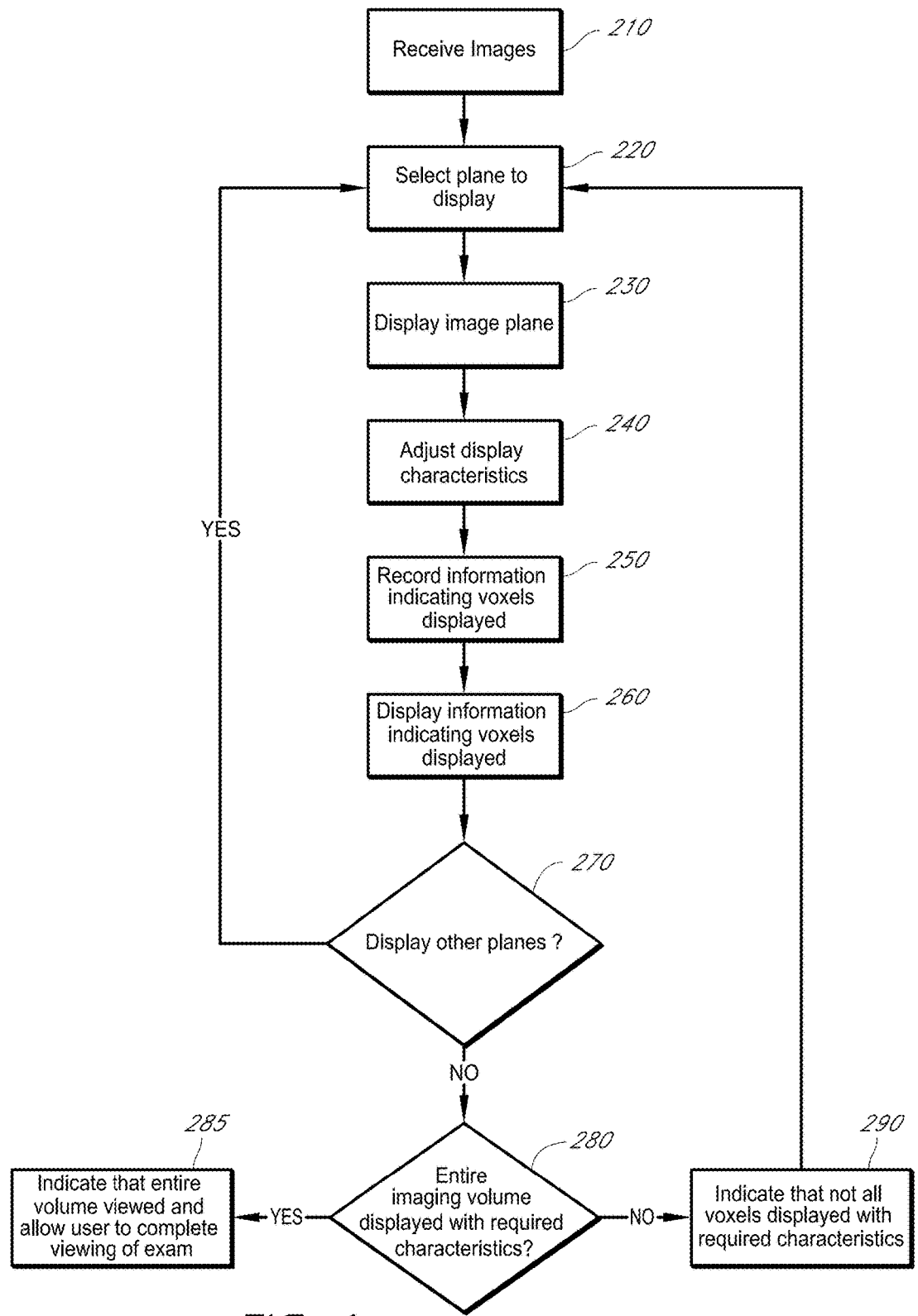
FIG. 4 is a flowchart illustrating a method of tracking which voxels of a medical imaging volume have been displayed according to user-defined display parameters.

FIG. 4 is a flowchart illustrating a method of tracking which voxels of a medical imaging exam have been displayed according to user-defined display parameters. More particularly, the exemplary method of FIG. 4 may be used to track which voxels of an imaging volume have been displayed by the physician, regardless of the plane of viewing, and provide feedback to the physician indicating whether the exam has been completely viewed. As noted above, it may be important and/or required that a user view all of a medical imaging volume at full resolution, or accordingly to other user-defined display parameters. The method described with reference to FIG. 4 is an example of one method of automatically tracking the portions of a 3D imaging volume, such as the voxels, that have already been displayed at full resolution, notating those portions, and providing the user with information indicating what portions of the imaging volume have been displayed at full resolution. This process is generally referred to as "voxel tracking." In an advantageous embodiment, the user interface provides a real time status of what portions of the imaging volume have been displayed at full resolution, or according to other user-defined display parameters.

In one embodiment, the method described with respect to FIG. 4 is performed by a computing system 100, a medical facility 190, or an image server 180, for example. For ease of description, the method will be discussed below with reference to a computing system 100 performing the method. Depending on the embodiment, certain of the blocks described below may be removed, others may be added, and the sequence of the blocks may be altered.

In one embodiment, the user-defined display parameters specify that an entire medical imaging volume must be viewed at full resolution before a reader may mark the image as read. However, the user-defined display parameters may have different requirements, such as requiring that at least a defined portion of the voxels are displayed at full resolution and/or a defined portion of the voxels are viewed with a certain display method, for example. In another embodiment, the user-defined display parameters may specify that the imaging volume be viewed at a resolution that is less than full resolution. In other embodiments, the user-defined display parameters may specify additional display settings that must be satisfied in order to allow the reader to mark the imaging volume as read. For example, the display parameters may be set to require that every $n^{th}$ voxel, or a certain percentage of the total voxels of an imaging volume, are displayed. Thus, various user-defined display parameters may be established on a user, modality, or facility basis, for example. In one embodiment, such as when viewing CT images, the display parameters may specify that the CT images are viewed using a specified series of display parameters, such as lung windows, bone windows, and/or other types of windows, for example. In this embodiment, if the user forgets to view the images separately using all the required display parameters, the CT images may be misinterpreted.

For ease of description, the following description refers to user-defined display parameters specifying that every voxel of the imaging volume is displayed at full resolution before it may be marked as read. However, the methods described herein are not limited to these display parameters and application of these methods using other user-defined display parameters is expressly contemplated. Any reference to tracking voxels at full resolution should be interpreted to cover similar systems and methods for monitoring and/or tracking of any other user-defined display parameter or combination of display parameters.

In one embodiment, the computing system 100 is configured to determine a portion of the imaging volume on which voxel tracking is to be applied. Many imaging volumes comprise regions outside the area of interest that are not important for a user, such as a doctor, to view and mark as read. For example, the imaging volume that results from a CT scan of the brain will include air outside of the head that is irrelevant to the analysis by the user. Accordingly, viewing of these irrelevant portions of the imaging volume according to the user-defined display parameters is not necessary. In one embodiment, the computing system 100 analyzes the medical image and determines those regions that are irrelevant to the user's analysis. These irrelevant regions are then excluded from the user-defined display parameters and a viewer may mark an image as read without viewing the irrelevant areas at full resolution, for example. In another embodiment, the user may define the irrelevant regions of an imaging volume prior to viewing portions of the image at full resolution. For example, the user may use the keyboard, mouse, or other input device, to select regions surrounding the volume of interest that do not require viewing according to the user-defined display parameters. In yet another embodiment, the user may determine that the relevant regions of an imaging volume have been viewed according to the display parameters, without the need to pre-select portions that should be viewed according to the display parameters. By providing for automatic and/or manual selection of irrelevant portions of a medical imaging volume, the viewer is not required to display those irrelevant portions of the medical imaging volume according to the user-defined display parameters, such as full resolution.

Returning to FIG. 4, in a block 210, a series of source images that make up an imaging volume are received from an image source. The image source may comprise one or more of the imaging devices 170, the image server 180, the medical facility 190, or any other device that is capable of transmitting medical images. The medical images may be received via the network 160, or by other means, such as transferred on a floppy disk, CD-ROM, or USB storage device. In certain embodiments, the received source images each comprise more pixels that the display device and, thus, an entire source image may not be concurrently displayed at full resolution. Commonly owned U.S. patent application Ser. No. 11/179,384 titled "Systems And Methods For Viewing Medical Images," which is hereby incorporated by reference in its entirety, describes exemplary systems and methods of tracking portions of 2D images that have been displayed according to user-defined display parameters. Images of an imaging volume, either source images or reformatted images, may be tracked using the systems and methods described in that application so that relevant portions of each image are displayed according to the user-defined display parameters.

Continuing to a block 220, a plane through the imaging volume is selected for display on the display device. As discussed above, the source images of the imaging volume may not be of a plane that the viewer wishes to view. For example, as described above with respect to FIG. 3, detection of certain features or abnormalities in an imaging space may be more easily detectable in certain planes, which may not be the plane of the source images. Accordingly, in certain embodiments, the user may select a plane of view in which reformatted images will be generated and displayed. In one embodiment, reformatted images are generated using the process of multiplanar reformatting. However, other methods of reformatting portions of a 3D imaging space in order to form images from any plane of the imaging space may also be used in conjunction with the systems and methods described herein.

Moving to a block 230, at least a portion of one of images, e.g., source or reformatted images, is displayed on the display device. As noted above, in many embodiments, the source and reformatted images comprise more pixels than a display device is capable of displaying at full resolution. Accordingly, only a portion of the images may be concurrently displayed on the display device.

Moving to a block 240, the user can adjust the display characteristics of the image currently being viewed, for example by adjusting the window level and window width. In one embodiment, adjustments made to the display characteristics of the currently displayed image are made to other images of the imaging space. Accordingly, if a contrast, brightness, or color level, for example, of an image is adjusted, the remaining images in the imaging space may also be adjusted.

Continuing to a block 250, an indication of the portion of the imaging volume that is displayed at full resolution is recorded. For example, the voxels being displayed in the imaging plane may be recorded, such as by storing voxel information in a memory 130 of the computing system 100. Alternatively, the information regarding displayed voxels may be stored on a local mass storage device 120 or central server, such as the image server 180.

Figure 5:
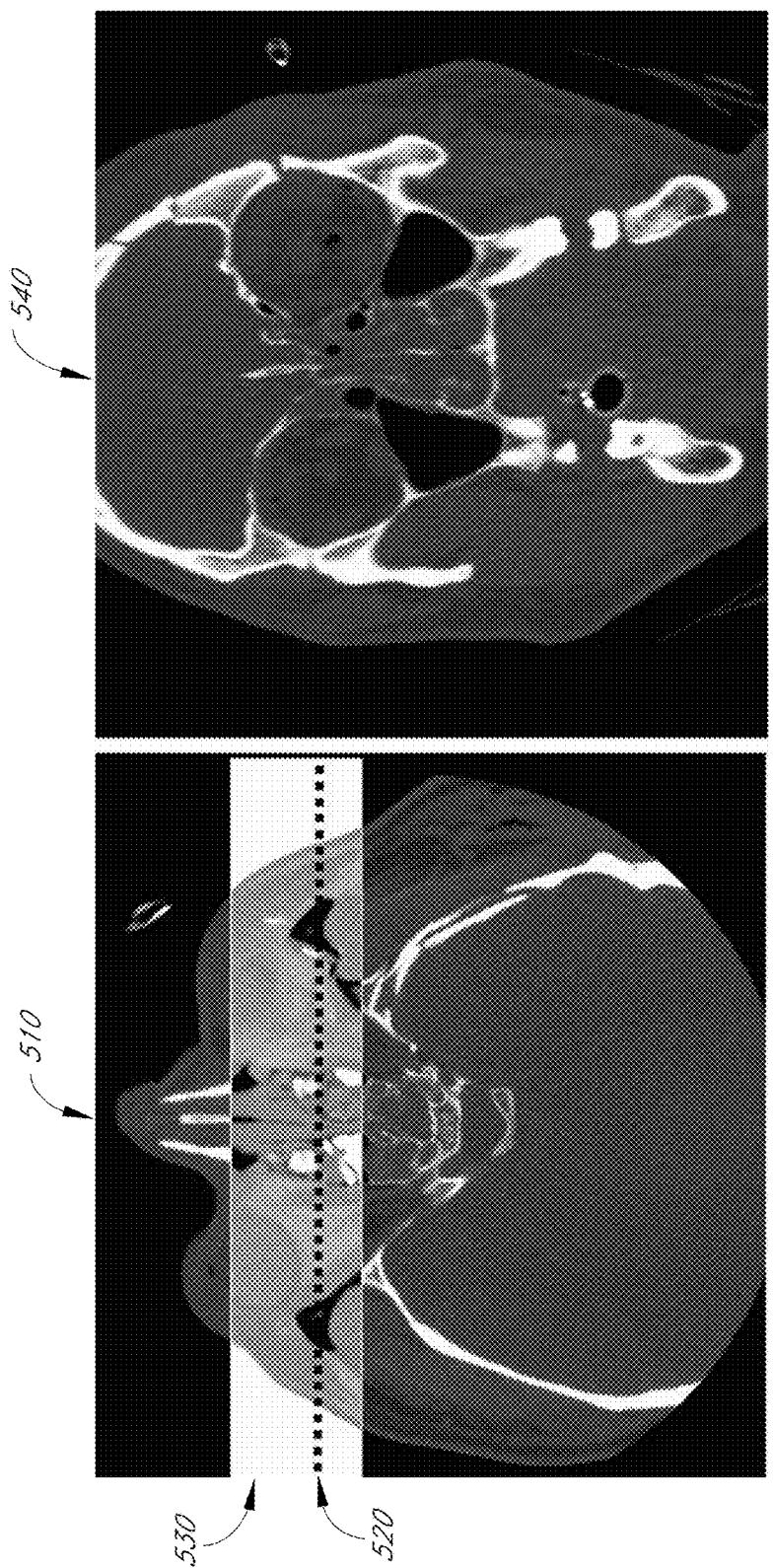
FIG. 5 illustrates portions of an exemplary graphical user interface (GUI) that may be displayed on a display device, either concurrently or separately.

Moving to a block 260, an indication of which regions of the imaging volume have been displayed at full resolution is displayed. For example, the user might interactively create a series of reformatted coronal images from a set of axial images that make up the imaging volume. One or more display characteristics of a reference axial image that the user has chosen could be altered to reflect voxels within that image that have been displayed at full resolution in one or more imaging planes, as illustrated in FIG. 5. Multiple references images might be displayed, for example in axial, coronal and sagittal orientations, each displaying an indication of which voxels have been displayed at full resolution along the corresponding planes. Alternatively, a three-dimensional cube might be displayed, with regions on each of three displayed faces that illustrate what voxels have been displayed at full resolution along the corresponding plane. For example, a user interface may include visual indications as to which portions of an imaging volume have not been displayed, or which voxels have not been displayed using a user-defined display parameter, such as a specified window or level setting. In one embodiment, the computing system 100 automatically displays a message indicating which regions of the imaging volume have not displayed with full pixel display and/or meeting user-defined display parameter criteria. In another embodiment, the computing system 100 automatically directs the user to any regions of the imaging volume that have not been displayed at full resolution and/or meeting user-defined display parameter criteria.

In one embodiment, the adjustment of a display characteristic to indicate regions that have or have not been displayed at full resolution comprises changing a color of the image portion. In another embodiment, other indicators, such as lines surrounding those image portions already displayed at full resolution, may be used to discriminate between portions of the imaging volume that have been displayed at full resolution and portions that have not been displayed at full resolution. Based on the distinguishing display characteristic, the user may select for display a portion of the imaging volume that has not yet been displayed at full resolution. In one embodiment, coloring of the viewed voxels may be toggled on and off by the user. In another embodiment, a text message, icon, or other indication, may be displayed at the bottom of the display, for example, indicating that the imaging volume has been viewed according to the user-defined display parameters. In yet another embodiment, the outside margins of the viewing pane may change color or the system could beep or provide some other audible feedback when the imaging volume has been displayed according to the user-defined display parameters.

In a decision block 270, the computing system 100 determines if another plane of the imaging volume has been selected for display at full resolution. In one embodiment, the user is presented with a full or reduced resolution representation of certain images within the imaging volume, for example axial, coronal and sagittal images through the middle of the imaging volume. Selection of a plane to be displayed using multiplanar reformatting may be accomplished by pressing certain keys on a keyboard, such as the arrow keys, for example. In another embodiment, the user may change the selected portion for viewing by moving a mouse, or other input device. In another embodiment, the computing system 100 may be configured to periodically update the display with a plane of the imaging volume that has not yet been displayed at full resolution, or update the display in response to an input from the user.

If in the decision block 270, the computing device 100 determines that instructions have been received to display another portion of the imaging volume on the display device, the method returns to block 220 where the image plane to be displayed is selected. The method then repeats the steps 220, 230, 240, 250, 260, and 270, allowing the user to view various portions of the imaging space by viewing reformatted images from various planes, and tracking which voxels of the imaging space have been viewed by the user. Because information indicating which voxels of the imaging space have been displayed according to the user-defined display parameters is stored by the computing system, the user can advantageously track the portions of the image space that have been viewed.

Referring again to the decision block 270, if the computing device 100 determines that instructions to display another portion of the imaging volume have not been received, the method continues to a decision block 280, wherein the computing device 100 determines whether all of the voxels in the imaging volume have been displayed at full resolution. If it is determined that not all of the voxels in the imaging volume have been displayed at full resolution, the method continues to a block 290, wherein an indication, such as an audible or visual alert, is provided to the user that not all of the voxels in the imaging volume have been viewed at full resolution. The method then returns to block 220. In one embodiment, the computing system 100 automatically selects an image, either a source image or reformatted image, for display from the portion of the imaging space that have not yet been displayed at full resolution, and/or that have not been displayed such that user-defined display parameters have been met.

If, however, in the decision block 280, the computing device 100 determines that the entire image has been displayed at full resolution, the method continues to a block 285, wherein an indication, such as an audible or visual alert, is provided to the user that the entire imaging volume have been displayed at full resolution. In certain embodiments, the user is only able to mark the imaging volume as read when the method reaches block 285.

As noted above, the flowchart of FIG. 4 illustrates an exemplary process of tracking voxels viewed by a user according to exemplary user-defined display parameters. In particular, the user-defined display parameters in the example of FIG. 4 specify that the entire imaging volume is viewed at full resolution. However, in other embodiments the user-defined display parameters may require that, for example, only a portion of the imaging volume is displayed at full resolution, or any other predetermined reduced resolution. In one embodiment, the user or the software may select portions of the imaging volume that must be displayed according to the user-defined display parameters. In another embodiment, the display parameters may specify that the viewer determines when the imaging volume has been viewed according to the user-defined display parameters. In this embodiment, the system may track the viewed voxels of the imaging volume, present the viewer with a view of the imaging volume that distinguishes portions of the imaging volume that have not been viewed at full resolution, or according to any other user-defined display parameters, and the viewer can determine whether the image can be marked as read.

In one embodiment, the user can establish user-defined display parameters and store those parameters in a database. In certain embodiments, rules may be established and linked to an individual user, user type, exam type, modality, or system, for example. These rules may trigger voxel tracking when certain events occur, such as a particular user opens an imaging space for viewing. In certain embodiments, rules may designate that voxel tracking applies to only certain viewers or users. In one embodiment, one set of display parameters can apply to one modality and another set of display parameters can apply to another modality. In addition, the rules may include specific triggers or warnings that occur if the user-defined display parameters are not satisfied. In one embodiment, the rules may indicate that the computing system 100 automatically direct the user to any voxels that have not been displayed with specific user-defined display parameters when the user attempts to mark an imaging space as read.

In one embodiment, the user is not able to notate an imaging volume as being read, or completely viewed, until the entire imaging volume has been displayed at full resolution. Accordingly, in the exemplary method of FIG. 4, if not all of the imaging volume has been displayed at full resolution, the method indicates that the entire imaging volume has not been viewed at full resolution in block 290, and the method returns to block 220, wherein another portion of the imaging volume may be selected for viewing.

It is noted that medical imaging exams can be subclassified into exam types. For example, "CT of the Brain" or "MRI of the Knee" may be exam types. Exam types can also be grouped into exam groups. For example, a user using the computing system 100 can indicate that two different exam types, such as "CT of the Chest" and "MRI of the Chest" belong in the same exam group, or that "CT of the Chest" and "CT of the Abdomen" belong in the same group. A user can also, via the system 100, set up rules related to voxel tracking that are linked to the exam group and/or modality and/or exam type or even per other exam specifiers. Thus, a user may require that all exams of a certain type or group are tracked according to user-defined rules, e.g., to determine if every voxel is displayed, and/or if every voxel is displayed with a bone window setting, etc. The rules can also be applied under other user-defined conditions, e.g., the referring doctor is an oncologist or if the exam indications are for cancer evaluation.

Similarly, users can also be grouped into user roles or user groups. A particular user or user having a user role may: (1) require a warning if the specified voxel tracking rules are not met (but still allow the user to mark the exam as "read"), (2) require that the rules are met before the exam is marked as "read", and\or (3) display a warning or track displayed data even if the user does not have the right to mark the exam as "read." The computing system 100 may also provide users guidance information. Voxel tracking might also be useful for a researcher or administrator who is studying the behavior of reading or viewing health care professionals.

FIG. 5 illustrates portions of an exemplary graphical user interface (GUI) that may be displayed on a display device, either concurrently or separately. More particularly, the exemplary GUI may display a reference image 510 that allows the user to select an image plane for viewing using the user-defined display parameters. In the embodiment of FIG. 5, the reference image 510 comprises a brain CT. A navigation line 520 may be adjusted by the user in order to move to another imaging plane. In one embodiment, as the user moves the navigation line, such as by using a mouse connected to the computing system 100, the computing system 100 generates 2D images perpendicular to the navigation line 520 using MPR (multiplanar reformatting), e.g., in the coronal orientation. The reformatted image 540 corresponding to the navigation line 520 is displayed in another portion of the GUI or, alternatively, may replace the navigation image 510. In one embodiment, the navigation image 510 is displayed in a pane of the GUI that is smaller than a pane that displays a corresponding reformatted image. In another embodiment, the navigational image 510 may be alternatively displayed on the display device so that more of the images may be concurrently displayed, for example. In the embodiment of FIG. 5, a contrast inverted region 530 of the navigation image 510 indicates the portions of the imaging volume that have been displayed according to the user-defined display parameters, such as full pixel resolution. Thus, the user can determine which portions of the imaging volume have been viewed according to the user-defined display parameters by noting the portions of the navigation image 510 that is within the inverted region 530. As noted above, other methods of indicating portions of the imaging space that have been displayed may also be used.

Figure 6:
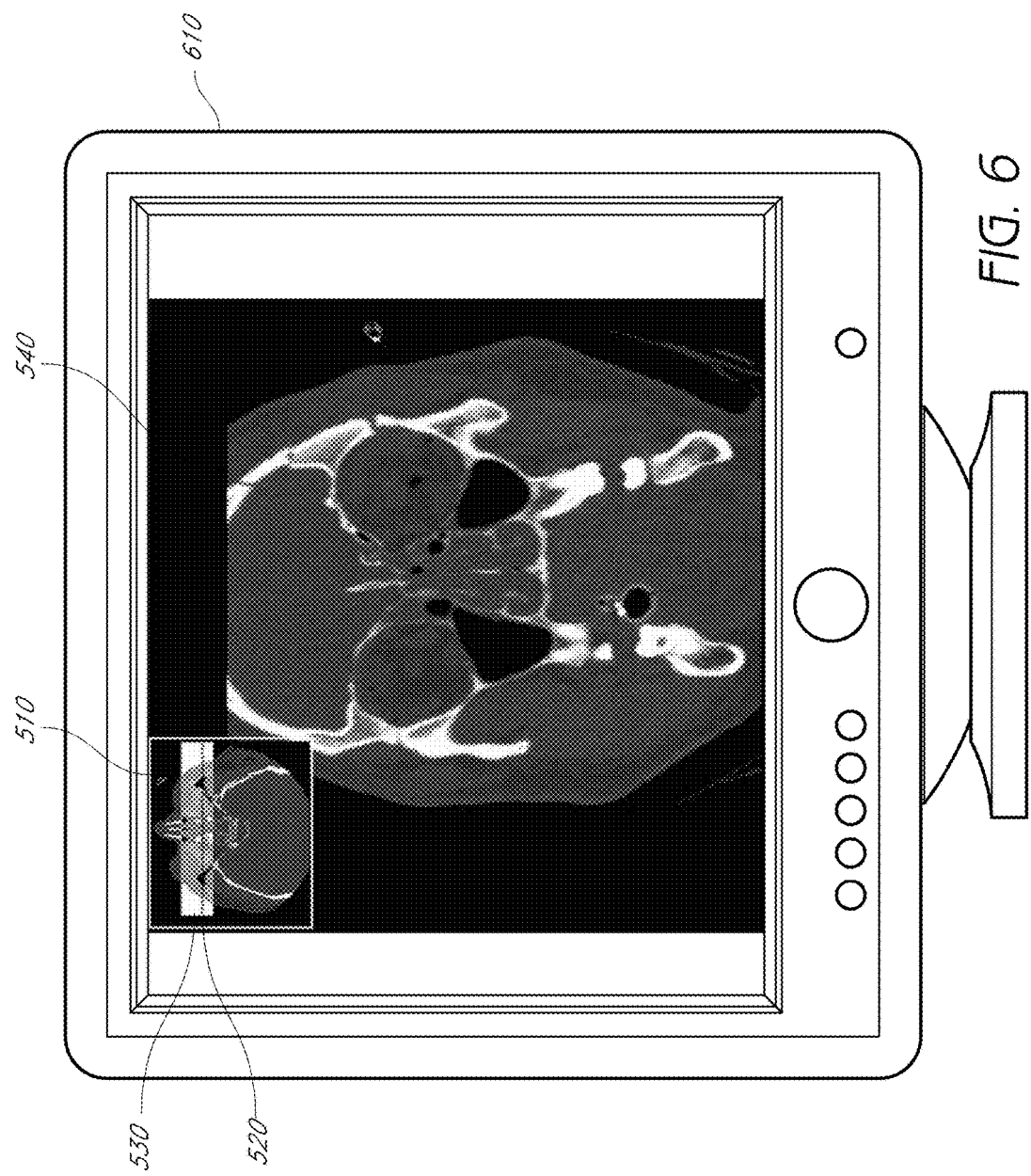
FIG. 6 illustrates a display device displaying a navigation image and a reformatted image representative of a cross-section of the imaging space at the location of a navigation line on the navigation image.

FIG. 6 illustrates a display device 610 displaying the navigation image 510 and the reformatted image 540. As noted above, the reformatted image 540 is a cross-section of the imaging space at the location of the navigation line 520 on the navigation image 510. In the embodiment of FIG. 6, as the user moves the navigation line 520 up and down the navigation image 510, the reformatted image 540 is replaced with other reformatted images corresponding to the current location of the navigation line 520. In this embodiment, the user can see which portions of the imaging volume have already been viewed while viewing portions of the imaging volume in another plane. In other embodiments, the navigation line 520 is oriented vertically, or at any other orientation, so that the user may cause generation of reformatted images in any plane desirable.

In another embodiment, multiple navigation images may be displayed on the display device 610. For example, two navigation images comprising orthogonal planes of the imaging volume may be concurrently displayed on the display device 610 and may provide the viewer with additional information regarding the location of the reformatted images displayed on the display device 610. In other embodiments, three or more navigation images from different planes of the imaging volume may be concurrently, or alternatively, displayed on the display device 610.

The foregoing description details certain embodiments of the invention. It will be appreciated, however, that no matter how detailed the foregoing appears in text, the invention can be practiced in many ways. For example, the above-described pixel checking method may be performed on other types of images, in addition to medical images. For example, images of circuit boards, airplane wings, geology, and satellite imagery may be analyzed using the described systems and methods for monitoring whether a three dimensional imaging volume has been viewed according to predefined display parameters. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computing system comprising:
a computer readable storage medium having program instructions embodied therewith; and
one or more processors configured to execute the program instructions to cause the one or more processors to:
determine, for a three dimensional imaging volume comprising a plurality of voxels, a subset of voxels from the plurality of voxels to be displayed, wherein the subset of voxels is represented as at least one of: a particular percentage of the plurality of voxels are to be displayed, or particular portions of the plurality of voxels are to be displayed, and wherein the subset of voxels is based on one or more of: a resolution of the three dimensional imaging volume, a user of the computing system, a type of user of the computing system, a modality of the three dimensional imaging volume, an exam type associated with the three dimensional imaging volume, a group of exams of which the three dimensional imaging volume is a part, a group of users of the computing system of which the user is a member, a facility in which the three dimensional imaging volume is displayed, or a system on which the three dimensional imaging volume is displayed;
receive indications of portions of the three dimensional imaging volume that are selectively displayed; and
determine whether the subset of voxels has been displayed based on the indications of portions of the three dimensional image volume that have been selectively displayed.

2. The computing system of claim 1, wherein the subset of voxels is based on a user the three dimensional imaging volume is displayed to.

3. The computing system of claim 1, wherein the subset of voxels is based on an exam type associated with the three dimensional imaging volume.

4. The computing system of claim 1, wherein the one or more processors are configured to execute the program instructions to further cause the one or more processors to:
in response to determining that the subset of voxels has not been displayed based on the indications of portions of the three dimensional imaging volume that have been selectively displayed, provide a warning to a user.

5. A computer-implemented method comprising:
by one or more processors executing program instructions:
determining, for a three dimensional imaging volume comprising a plurality of voxels, a subset of voxels from the plurality of voxels to be displayed, wherein the subset of voxels is represented as at least one of: a particular percentage of the plurality of voxels are to be displayed, or particular portions of the plurality of voxels are to be displayed, and wherein the subset of voxels is based on one or more of: a resolution of the three dimensional imaging volume, a user of the computing system, a type of user of the computing system, a modality of the three dimensional imaging volume, an exam type associated with the three dimensional imaging volume, a group of exams of which the three dimensional imaging volume is a part, a group of users of the computing system of which the user is a member, a facility in which the three dimensional imaging volume is displayed, or a system on which the three dimensional imaging volume is displayed;

receiving indications of portions of the three dimensional imaging volume that are selectively displayed; and determining whether the subset of voxels has been displayed based on the indication of portions of the three dimensional imaging volume that have been selectively displayed.

6. The computer-implemented method of claim 5, wherein the subset of voxels is based on a user the three dimensional imaging volume is displayed to.

7. The computer-implemented method of claim 5, wherein the subset of voxels is based on an exam type associated with the three dimensional imaging volume.

8. The computer-implemented method of claim 5 further comprising:

by the one or more processors executing program instructions:

in response to determining that the subset of voxels has not been displayed based on the indications of portions of the three dimensional imaging volume that have been selectively displayed, providing a warning to a user.

9. A computer program product comprising a non-transitory computer readable storage medium having program instructions embodied therewith, the program instructions executable by one or more processors to cause the one or more processors to:

determine, for a three dimensional imaging volume comprising a plurality of voxels, a subset of voxels from the plurality of voxels to be displayed, wherein the subset of voxels is represented as at least one of: a particular percentage of the plurality of voxels are to be displayed, or particular portions of the plurality of voxels are to be displayed, and wherein the subset of voxels is based on one or more of: a resolution of the three dimensional imaging volume, a user of the computing system, a type of user of the computing system, a modality of the three dimensional imaging volume, an exam type associated with the three dimensional imaging volume, a group of exams of which the three dimensional imaging volume is a part, a group of users of the computing system of which the user is a member, a facility in which the three dimensional imaging volume is displayed, or a system on which the three dimensional imaging volume is displayed;

receive indications of portions of the three dimensional imaging volume that are selectively displayed; and determine whether the subset of voxels has been displayed based on the indications of the portions of three dimensional imaging volume that have been selectively displayed.

10. The computer program product of claim 9, wherein the subset of voxels is based on a user the three dimensional imaging volume is displayed to.

11. The computer program product of claim 9, wherein the subset of voxels is based on an exam type associated with the three dimensional imaging volume.

12. The computer program product of claim 9, wherein the program instructions are executable by one or more processors to further cause the one or more processors to:

in response to determining that the subset of voxels has not been displayed based on the indications of portions of the three dimensional imaging volume that have been selectively displayed, providing a warning to a user.

* * * * *